(12) United States Patent
Traversari et al.

(10) Patent No.: US 7,413,733 B2
(45) Date of Patent: Aug. 19, 2008

(54) ANTIGEN TRANSDUCED T CELLS USED AS A DELIVERY SYSTEM FOR ANTIGENS

(75) Inventors: Catia Traversari, Milan (IT); Claudio Bordignon, Milan (IT)

(73) Assignee: MolMed SpA, Milan (IT)

( * ) Notice: Subject to any disclaimer, the term of this patent is extended or adjusted under 35 U.S.C. 154(b) by 318 days.

(21) Appl. No.: 10/492,143

(22) PCT Filed: Oct. 21, 2003

(86) PCT No.: PCT/IB03/05109

§ 371 (c)(1),
(2), (4) Date: Apr. 9, 2004

(87) PCT Pub. No.: WO2004/035768

PCT Pub. Date: Apr. 29, 2004

(65) Prior Publication Data

US 2004/0235172 A1  Nov. 25, 2004

(30) Foreign Application Priority Data

Oct. 21, 2002 (GB) .................................. 0224442.4

(51) Int. Cl.
*A01K 63/00* (2006.01)
(52) U.S. Cl. .................... 424/93.21; 424/93.1; 424/93.2
(58) Field of Classification Search ........................ None
See application file for complete search history.

(56) References Cited

U.S. PATENT DOCUMENTS

| | | | |
|---|---|---|---|
| 4,663,058 A | 5/1987 | Wells et al. | 210/801 |
| 5,139,941 A | 8/1992 | Muzyczka et al. | 435/456 |
| 5,797,368 A | 8/1998 | Kreuter et al. | 123/308 |

FOREIGN PATENT DOCUMENTS

| | | |
|---|---|---|
| EP | 0 904 786 | 3/1999 |
| EP | 0 905 786 | 3/1999 |
| EP | 1 148 066 A1 | 10/2001 |
| WO | WO 95/31208 | 11/1995 |
| WO | WO 96/01126 | 1/1996 |
| WO | WO 97/19169 | 5/1997 |

OTHER PUBLICATIONS

Strobel et al, Hum Gene Ther 2000;11:2207-18.*
McWilliams et al, J Immunol 2006;177:155-61.*
Powell et al, J Immunol 2006; 177(9):6527-39.*
Yu & Restifo, J Clin Invest Aug. 2002;110:289-94.*
Bodey et al, Anticancer Res 2000;20:2665-76.*
Janeway et al, Immunobiol 2001, see Particularly Part IV,§ 8.*
Cebon et al, Austral J Dermatol 1997;58:S66-72.*
Mathisen et al., Brief Definitive Report; Treatment of Experimental Autoimmune Encephalomyelitis With Genetically Modified Memory T Cells; vol. 186, No. 1, Jul. 7, 1997; pp. 159-164.
WPIDS Abstract Accession No. 2003-046799/200304 and Related Publication Jan. 2007. WO 2002/079253A; Cancer Antigen WTI Modified Peptides and DNA Encoding Them For Cancer Immunotherapy; Inventor: H. Sugiyama; Oct. 2004.
Bordignon et al., *Haematologica*, 84(12):1110-1149 (1999).
International Search Report in PCT/IB03/05109 dated Mar. 1, 2004.
Introna et al., *Hum. Gene Ther.*, 11(4):611-620 (2000).
Riddell et al., *Nat. Med.*, 2(2):216-223 (1996).
Verzeletti et al., *Hum. Gene Ther.*, 9(15):2243-2251 (1998).
Yang et al., *J. Virol.*, 69(4):2004-2015 (1995).

* cited by examiner

*Primary Examiner*—Q. Janice Li
(74) *Attorney, Agent, or Firm*—Marshall, Gerstein & Borun LLP

(57) ABSTRACT

A delivery system comprising a T cell comprising at least one antigen capable of loading antigen-presenting-cells with the antigen.

11 Claims, 7 Drawing Sheets

US 7,413,733 B2

ANTIGEN TRANSDUCED T CELLS USED AS A DELIVERY SYSTEM FOR ANTIGENS

FIELD OF THE INVENTION

This application is U.S. National Phase Application pursuant to 35 U.S.C. 371 of International Application No. PCT/IB03/05109 which was filed Oct. 21, 2003, claiming benefit of priority of Great Britain Patent Application No. 0224442.4 filed Oct. 21, 2002. The entire disclosure of each of the foregoing applications is incorporated herein by reference.

The present invention relates to a delivery system for an antigen in the form of a T cell, the use of such a T cell to monitor an immune response and a method of preparing the T cell.

BACKGROUND OF THE INVENTION

Gene transfer into human cells is being investigated for the treatment of a variety of genetic and acquired human diseases. Genetic diseases, due to a single-gene defect, were originally proposed as the primary targets of gene therapy. However, the majority of the human gene therapy trials approved so far involve treatment of acquired diseases, such cancer and AIDS. One approach to tumor gene therapy relies on the stimulation of the host immune system against tumor antigens by vaccination of the patient with genetically modified tumor cells, in which the transgene (cytokine, allo-HLA, etc.) is aimed at boosting their immunogenicity. An alternative approach is based on the adoptive transfer of ex vivo generated tumor-specific effectors. The infused effectors are usually autologous or HLA-compatible lymphocytes stimulated in vitro to proliferate by specific as well as non-specific stimuli. Amplification of the effector function of the infused cells has been achieved by their transduction with cytokine-encoding genes.

EP 0 904 786 discloses a method of tumor vaccination with at least two subsequent administrations of a compositions consisting essentially of autologous or HLA-related cells which are capable of presenting antigen in a patient, said cells being either tumor cells transduced with a foreign gene or antigen presenting cells transduced with a tumor antigen and a foreign antigen.

WO97/19169 discloses a tumor vaccine containing tumor cells at least a portion of which has at least one MHC-I haplotype of the patient on the cell surface, and which have been loaded with an antigen.

Thus, the prior art takes the approach of using a tumor cell as the delivery system for an antigen, or an antigen presenting cell which is understood as presenting the antigen directly to a T cell.

It will be however appreciated that there is a continuing need to provide vaccines and vaccination approaches. The present invention provides such an approach.

SUMMARY OF THE INVENTION

The present invention relates to manipulated T cells that when introduced into a patient are able to bring antigens, such as tumor, bacterial or viral antigens, into contact with professional antigen presenting cells (APCs). More particularly, the invention provides a transduced T cell containing an exogenous (or foreign) gene encoding an antigen to stimulate a response against the antigen, and T cell loaded with an antigenic polypeptide to stimulate a response. The T cell may also comprise a further antigen such as HSV-Tk which may be used to monitor vaccination effectiveness. Conveniently the T cells are prepared in vitro and when injected, or otherwise introduced in vivo, carry the transgene products to professional antigen presenting cells, thus stimulating the immune response against the transgene product. The invention also provides a methodology whereby one can monitor the immunological status of the patient. The present invention further provides a culturing method for T cells.

Thus, we have now found that T cells containing an antigen act to bring the antigen to an antigen presenting cell (APC), such that the APC subsequently presents the antigen to generate an immune response. The present invention therefore employs a different strategy to the prior art.

STATEMENTS OF THE INVENTION

According to one aspect of the present invention there is provided a delivery system comprising a T cell comprising at least one antigen and capable of delivering the antigen to a lymph node, or other part of the lymph system.

In other words the present invention provides a delivery system comprising a T cell comprising at least one antigen capable of loading antigen presenting cells (APCs) with the antigen.

The antigen is generally foreign to the T cell. By "foreign" we include antigens which are normally exogenous to the T cell.

The antigen may be introduced into the T cell as a polynucleotide encoding the antigen, i.e. the T cell may be transfected or transduced with the polynucleotide, or the T cell may be loaded with the antigen in the form of a polypeptide, but may equally well be a protein. For ease of reference, the terms polypeptide and protein and generally used interchangeably throughout. Thus, by the T cell comprising the antigen we mean that the antigen is associated with the T cell such that the T cell is capable of delivering the antigen to the lymph node and/or APCs.

According to another aspect of the present invention there is provided a delivery system comprising a T cell comprising at least one antigen and capable of delivering the antigen to an APC for subsequent presentation by the APC.

In one embodiment the foreign antigen is a bacterial or viral antigen. Preferably the foreign antigen is a tumor antigen.

Preferably the T cell is further comprises at least one further foreign polypeptide or polynucleotide sequence.

In one embodiment the further foreign gene is a marker, i.e. a marker or selection gene.

Preferably the marker is a bacterial resistance gene, e.g. a bacterial resistance gene which confers neomycin resistance.

In another embodiment the marker is a further antigen, preferably HSV-Tk or CD20. This antigen are particularly preferred because they can be employed in so-called suicide systems.

In a further embodiment the delivery system further comprises both the further antigen and marker gene.

Preferably the T cell expresses at least one of the following markers: HLA-I, HLA-II CD80, CD86, CD27, CD40L, CD62L, CCR7, CD54 and CD25.

Thus, in another aspect of the present invention there is provided a T cell which expresses at least one of the following markers: HLA-I, HLA-II, CD80, CD86, CD27, CD40L, CD62L, CCR7, CD54 and CD25.

According to another aspect of the present invention there is provided use of a T cell comprising at least two antigens capable of raising an immune response, and wherein the response against one of the antigens is used for monitoring the immune response against the other antigen.

According to another aspect of the present invention there is provided a method of monitoring the immune response to a T cell containing a first antigen capable of raising an immune response, comprising introducing a second antigen into the T cell.

According to another aspect of the present invention there is provided a method of loading APCs in vivo comprising exposing the APCs to a T cell containing an antigen.

According to yet another aspect of the present invention there is provided a method of obtaining a T cell for use in the method of claim comprising
isolating a T cell;
activating the T cell;
culturing the T cell;
introducing an antigen into the T cell.

Preferably the T cell is transduced or transfected with a polynucleotide sequence coding for the antigen.

Preferably the T cell is activated with phytoemoagglutinine, anti-CD3 monoclonal antibody or anti-CD3/CD28 monoclonal antibody-coated beads.

Preferably the T cell is cultured in the presence of growth factors, such as hu-r-IL-2.

Preferably the T cell is cultured in a culture media which comprises 5% autologous serum.

Preferably the T cell is cultured at $1\times10^6$ cells/ml.

According to a further aspect of the present invention there is provided a T cell obtainable by the process of the present invention, and which is useful as a delivery system according to the present invention.

DETAILED DESCRIPTION OF THE INVENTION

Various preferred features and embodiments of the present invention will now be described by way of non-limiting example.

Although in general the techniques mentioned herein are well known in the art, reference may be made in particular to Sambrook et al., Molecular Cloning, A Laboratory Manual (1989) and Ausubel et al., Short Protocols in Molecular Biology (1999) $4^{th}$ Ed, John Wiley & Sons, Inc (as well as the complete version Current Protocols in Molecular Biology).

In general terms the present invention relates to in vitro manipulated T lymphocytes (T cells) that when injected in vivo are able to carry antigens (e.g. tumor, bacterial or viral antigens) into contact with professional antigen presenting cells. However, the present invention also encompasses in vivo manipulation of T cells. More particularly, the invention relates to: a) in vitro transduced/transfected T lymphocytes containing exogenous genes encoding a tumor antigen, to stimulate the immune response against the tumor; and b) T lymphocytes loaded in vitro with peptides encoding tumor antigen epitopes. The T cells may also comprise a further strong antigen, e.g. HSV-Tk, to monitor vaccination effectiveness.

It has been reported that T cells are suitable targets for gene transfer through, e.g. retroviral vectors. In particular the use of T cells expressing tumor antigens for tumor vaccination has been described. However, it has also been reported, e.g. in EP 0 905 786, that the any effect occurs through T cells acting as antigen presenting cells (APCs). In contrast to this view we have now found that the T cells act by exposing an APC to the transgene which is subsequently presented by the APC. In other words, the T cells expose the transgene product to an APC for antigen processing and presentation. By "exposing" we include bringing the transgene into contact with an APC such that binding and/or uptake of the transgene product occurs. The APC internalises the antigen and processes it for presentation.

By "antigen processing" we include the degradation of the antigen into shorter peptide sequences and the association of the peptide with MHC molecules. Two distinct classes of MHC molecules, MHC class I and MHC class II, regulate the presentation of antigens to either CD8+ or CD4+ T cells, respectively. Antigen presentation is, strictly speaking, the activation of T cells via T cell receptors, which specifically recognise antigenic peptide in association with either MHC class I or class II molecules on the surface of APCs; however B cells are also capable of recognising and binding certain antigens.

We have also found that the present system provides an effective method of delivering an antigen to the lymph system, and particularly the lymph nodes. The T cells may be administered locally, but we also believe that the T cells are capable of efficiently migrating to the lymph nodes, even if they are administered at a distal site. Lymph nodes function as an immunologic filter for the bodily fluid known as lymph. Lymph nodes are found throughout the body. Composed mostly of T cells, B cells, dendritic cells and macrophages, the nodes drain fluid from most of our tissues. Antigens are filtered out of the lymph in the lymph node before returning the lymph to the circulation. In a similar fashion in the spleen, the macrophages and dendritic cells that capture antigens present these foreign materials to T and B cells, consequently initiating an immune response.

The invention further thus provides a cell-dependent delivery system for an antigen. In this system the antigen, or a polynucleotide encoding the antigen, is introduced into one or more cells ex vivo and then introduced into the patient.

The T cells of the present invention may be administered alone, but will generally be administered as a pharmaceutical composition.

APCs and Immune Response

As mentioned above the present invention relates to delivery of an antigen to an antigen presenting cell (APC). APCs include macrophages, dendritic cells, B cells and virtually any other cell type capable of expressing an MHC molecule.

Macrophages are phagocytic cells of the monocytic lineage residing within tissues and are particularly well equipped for effective antigen presentation. They generally express MHC class II molecules and along with their phagocytic properties are extremely efficient at engulfing macromolecular or particulate material, digesting it, processing it with an extensive lysosomal system to antigenic peptide form, and expressing it on the cell surface for recognition by T lymphocytes.

Dendritic cells, so named for their highly branched morphology, are found in many organs throughout the body, are bone marrow-derived and usually express high levels of MHC class II antigen. Dendritic cells are actively motile and can recirculate between the bloodstream and tissues. Dendritic cells are antigen-presenting-cells with a unique ability to induce primary immune responses, thus permitting establishment of immunological memory. Dendritic cells in the immature state have an high phagocytic capacity. After antigen capture, immature dendritic cells migrate to the lymph nodes where, after maturation, activate circulating antigen-specific lymphocytes. In this way, they too are considered important APCs. Langerhans cells are an example of dendritic cells that are located in the skin.

B lymphocytes, while not actively phagocytic, are class II-positive and possess cell surface antigen-specific receptors, immunoglobulin, or antibody molecules. Due to their potential for high affinity antigen binding, B cells are uniquely endowed with the capacity to concentrate low concentrations of antigen on their surface, endocytose it, process it and present it in the context of antigenic peptide in association with MHC antigen on their surface. In this manner, B cells become extremely effective APCs.

Thus, an immune response to foreign antigen requires the presence of an antigen-presenting cell (APC) (usually either a macrophage or dendritic cell), in combination with a B cell or T cell. When an APC presents an antigen on its cell surface to a B cell, the B cell is signalled to proliferate and produce antibodies that specifically bind to that antigen. If the antibodies bind to antigens on bacteria or parasites it acts as a signal for polymorphonuclear leukocytes or macrophages to engulf (phagocytose) and kill them. Another important function of antibodies is to initiate the "complement destruction cascade". When antibodies bind to cells or bacteria, serum proteins called complement bind to the immobilized antibodies and destroy the bacteria by creating holes in them. Antibodies can also signal natural killer cells and macrophages to kill viral or bacterial-infected cells.

If the APC presents the antigen to T cells, the T cells become activated. Activated T cells proliferate and become secretory in the case of CD4+ T cells, or, if they are CD8+ T cells, they become activated to kill target cells that specifically express the antigen presented by the APC. The production of antibodies and the activity of CD8+ killer T cells are highly regulated by the CD4+ helper T cell subset. The CD4+ T cells provide growth factors or signals to these cells that signal them to proliferate and function more efficiently.

T Cells

T cells or T lymphocytes are usually divided into two major subsets that are functionally and phenotypically (identifiably) different. The T helper subset, also called the CD4+ T cell, is a pertinent coordinator of immune regulation. The main function of the T helper cell is to augment or potentiate immune responses by the secretion of specialized factors that activate other white blood cells to fight off infection.

Another important type of T cell is called the T killer-subset or CD8+ T cell. These cells are important in directly killing certain tumor cells, viral-infected cells and sometimes parasites. They often depend on the secondary lymphoid organs (the lymph nodes and spleen) as sites where activation occurs, but they are also found in other tissues of the body, most conspicuously the liver, lung, blood, and intestinal and reproductive tracts.

Where T cells are to be used in the ex vivo methods of the invention, the T cells are typically T lymphocytes isolated from the blood of a patient or donor. T cells are obtained by an appropriate method (e.g. as described in U.S. Pat. No. 4,663,058) and may be enriched and/or purified by standard methods including antibody-mediated separation. The T cells may be used in combination with other immune cells, obtained from the same or a different individual. Alternatively whole blood may be used or leukocyte enriched blood or purified white blood cells as a source of T cells and other cell types. It is particularly preferred to use helper T cells (CD4$^+$). Alternatively other T cells such as CD8$^+$ cells may be used. It may also be convenient to use cell lines such as T cell hybridomas, immature T cells of peripheral or thymic origin and NK-T cells. In a preferred embodiment, the T cells used in the present invention will be T cells that can transfer antigen specific suppression to other T cells.

Introduction of Polypeptides and Nucleic Acid Sequences into T Cells

Antigenic polypeptide substances may be administered to T cells as the polypeptide itself or by introducing nucleic acid constructs/viral vectors encoding the polypeptide into cells under conditions that allow for expression of the polypeptide in the T cell.

Preferably, a polynucleotide for use in the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors of the invention may be transformed or transfected into a T cell as described below to provide for expression of an antigen.

The present invention also encompasses T cells into which antigens, e.g. in the form of polypeptides, are introduced, i.e. loaded.

For ease of reference both the antigenic polypeptides and polynucleotides encoding therefor may be referred to as "antigen".

Convenient non-limiting methods for introducing both genes and polypeptides into T cells are discussed below.

Any suitable method of transforming the T cell may be used. Non-limiting examples of currently available mechanisms for delivery are via electroporation, calcium phosphate transformation or particle bombardment. However, transfer of the construct may be performed by any of the methods mentioned which physically or chemically permeabilize the cell membrane. Suitable methods are described in more detail below.

1. Electroporation

In certain preferred embodiments of the present invention, the antigen is introduced into the cells via electroporation. Electroporation involves the exposure of a suspension of cells and DNA to a high-voltage electric discharge.

It is contemplated that electroporation conditions for T cells may be optimized. One may particularly with to optimize such parameters as the voltage, the capacitance, the time and the electroporation media composition. The execution of other routine adjustments will be known to those of skill in the art.

2. Particle Bombardment

One method for transferring a naked DNA construct into cells involves particle bombardment. This method depends on the ability to accelerate DNA-coated microprojectiles to a high velocity allowing them to pierce cell membranes and enter cells without killing them. The microprojectiles used have consisted of biologically inert substances such as tungsten, platinum or gold beads.

It is contemplated that in some instances DNA precipitation onto metal particles would not be necessary for DNA delivery to a recipient cell using particle bombardment. It is contemplated that particles may contain DNA rather than be coated with DNA. Hence it is proposed that DNA-coated particles may increase the level of DNA delivery via particle bombardment but are not, in and of themselves, necessary.

Several devices for accelerating small particles have been developed. One such device relies on a high voltage discharge to generate an electrical current, which in turn provides the motive force. Another method involves the use of a Biolistic Particle Delivery System, which can be used to propel particles coated with DNA through a screen, such as stainless steel or Nytex screen, onto a filter surface covered with cells in suspension. The screen disperses the particles so that they are not delivered to the recipient cells in large aggregates. It is believed that a screen intervening between the projectile apparatus and the cells to be bombarded reduces the size of projectile aggregates and may contribute to a higher frequency of transformation by reducing the damage inflicted on the recipient cells by projectiles that are too large.

For the bombardment, cells in suspension are preferably concentrated on filters, or alternatively on solid culture medium. The cells to be bombarded are positioned at an appropriate distance below the macroprojectile stopping plate. If desired, one or more screens are also positioned between the acceleration device and the cells to be bombarded.

It is contemplated that one may wish to adjust various of the bombardment parameters in small scale studies to fully optimize the conditions. One may particularly wish to adjust physical parameters such as gap distance, flight distance, tissue distance and helium pressure. One may also optimize the trauma reduction factors by modifying conditions which influence the physiological state of the recipient cells and which may therefore influence transformation and integration efficiencies. For example, the osmotic state, tissue hydration and the subculture stage or cell cycle of the recipient T cells may be adjusted for optimum transformation. The execution of other routine adjustments will be known to those of skill in the art.

3. Viral Transformation a. Adenoviral Infection

One method for delivery of the nucleic acid constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a construct that has been cloned therein.

The vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb. In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off. The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins. Since the E3 region is dispensable from the adenovirus genome the current adenovirus vectors, with the help of 293 cells, carry foreign DNA in either the E1, the D3 or both regions. In nature, adenovirus can package approximately 105% of the wild-type genome, providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., 10.sup.9-10.sup.11 plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus, demonstrating their safety and therapeutic potential also as in vivo gene transfer vectors.

b. AAV Infection

Adeno-associated virus (AAV) is an attractive vector system for use in the present invention as it has a high frequency of integration and it can infect nondividing cells, thus making it useful for delivery of genes into mammalian cells in tissue culture. AAV has a broad host range for infectivity. Details concerning the generation and use of rAAV vectors are described in U.S. Pat. No. 5,139,941 and U.S. Pat. No. 4,797,368, each incorporated herein by reference.

Recombinant AAV vectors have been used successfully for in vitro and in vivo transduction of marker genes and genes involved in human diseases. Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells. In the absence of coinfection with helper virus, the wild type AAV genome integrates through its ends into human chromosome 19 where it resides in a latent state as a provirus rAAV, however, is not restricted to chromosome 19 for integration unless the AAV Rep protein is also expressed. When a cell carrying an AAV provirus is superinfected with a helper virus, the AAV genome is "rescued" from the chromosome or from a recombinant plasmid, and a normal productive infection is established.

Typically, recombinant AAV (rAAV) virus is made by cotransfecting a plasmid containing the gene of interest flanked by the two AAV terminal repeats and an expression plasmid containing the wild type AAV coding sequences without the terminal repeats, for example pIM45. The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used. Cell lines carrying the rAAV DNA as an integrated provirus can also be used.

c. Retroviral Infection

One preferred method of the present invention involves the use of retroviruses. The retroviral vector of the present invention may be derived from or may be derivable from any suitable retrovirus. A large number of different retroviruses have been identified. Examples include: murine leukemia virus (MLV), human immunodeficiency virus (HIV), simian immunodeficiency virus, human T-cell leukemia virus (HTLV). equine infectious anaemia virus (EIAV), mouse mammary tumor virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV). A detailed list of retroviruses may be found in Coffin et al., 1997, "retroviruses", Cold Spring Harbour Laboratory Press Eds: J M Coffin, S M Hughes, H E Varmus pp 758-763.

Details on the genomic structure of some retroviruses may be found in the art. By way of example, details on HIV and Mo-MLV may be found from the NCBI Genbank (Genome Accession Nos. AF033819 and AF033811, respectively).

Retroviruses may be broadly divided into two categories: namely, "simple" and "complex". Retroviruses may even be further divided into seven groups. Five of these groups represent retroviruses with oncogenic potential. The remaining two groups are the lentiviruses and the spumaviruses. A review of these retroviruses is presented in Coffin et al., 1997 (ibid).

The lentivirus group can be split even further into "primate" and "on-primate". Examples of primate lentiviruses include human immunodeficiency virus (HIV), the causative agent of human auto-immunodeficiency syndrome (AIDS), and simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells. In contrast, other retroviruses—such as MLV—are unable to infect non-dividing cells such as those that make up, for example, muscle, brain, lung and liver tissue.

Each retroviral genome comprises genes called gag, pol and env which code for virion proteins and enzymes. In the provirus, these genes are flanked at both ends by regions called long terminal repeats (LTRs). The LTRs are responsible for proviral integration, and transcription. LTRs also serve as enhancer-promoter sequences and can control the expression of the viral genes. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses. The basic molecular organisation of an infectious retroviral RNA genome is (5') R-U5-gag, pol, env-U3-R (3'). In a defective retroviral vector genome gag, pol and env may be absent or not functional. The R regions at both ends of the RNA are repeated sequences. U5 and U3 represent unique sequences at the 5' and 3' ends of the RNA genome respectively.

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. However, integration and stable expression require the division of host cells.

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination.

d. Other Viral Vectors

Other viral vectors may be employed as constructs in the methods and compositions described here. Vectors derived from viruses such as vaccinia and herpesviruses may be employed.

4. Calcium Phosphate Co-Precipitation or DEAE-Dextran Treatment

In other preferred embodiments, antigen is introduced to the cells using calcium phosphate co-precipitation. In another embodiment, the expression construct is delivered into the cell using DEAE-dextran followed by polyethylene glycol.

5. Direct Microinjection or Sonication Loading

Further embodiments include the introduction of the antigen by direct microinjection or sonication loading.

6. Liposome Mediated Transformation

In a further embodiment, the antigen may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. Also contemplated is a nucleic acid construct complexed with Lipofectamine (Gibco BRL).

In certain embodiments of the invention, the liposome may be complexed with a hemagglutinating virus (HVJ). This has been shown to facilitate fusion with the cell membrane and promote cell entry of liposome-encapsulated DNA. In other embodiments, the liposome may be complexed or employed in conjunction with nuclear non-histone chromosomal proteins (HMG-1). In yet further embodiments, the liposome may be complexed or employed in conjunction with both HVJ and HMG-1.

7. Adenoviral Assisted Transfection

In certain embodiments, the nucleic acid construct is introduced into the cell using adenovirus assisted transfection. Increased transfection efficiencies have been reported in cell systems using adenovirus coupled systems, and the inventors contemplate using the same technique to increase transfection efficiencies.

Culturing

The present invention also provides a method of culturing T cells for use in the present invention.

In particular, peripheral blood mononuclear cells (PBMC) isolated from peripheral blood may be activated in vitro to proliferate. Mitogenic stimulation may be obtained by the use of compounds such as phytoemoagglutinine (PHA; 2 µg/ml) or anti-CD3 mAb (OKT3; 30 ng/ml).

Activated T cells may be cultured at $1\times10^6$ cells/ml, in media supplemented with 5% autologous serum in the presence of growth factors, such as hu-r-IL-2 (e.g. 100 U/ml).

One preferred embodiment the T cells are cultured in the presence of magnetic beads coated with antibodies to CD3 and CD28, preferably in the presence of hu-r-IL2 (e.g. 100 U/ml). Conveniently the beads are used at a ratio of three beads/ T cell.

The T cells may then be transduced/transfected by exposure of the activated T cells e.g. using viral vector(s) encoding the antigen(s). The expression of the transgene(s) may be used to evaluate transduction efficiency. Selection genes and markers is discussed in more detail below. Alternatively, lymphocytes may cultured as described above, but not transduced/transfected. Instead, before administration to a patient, activated T cells are loaded with antigen, e.g. in the form of synthetic peptides encoding e.g. well-known tumor, bacterial or viral antigens The entire manipulation process generally lasts 5-15 days.

The manipulated T cells may be frozen for storage purposes.

At the end of the culture the manipulated T cells should express at least one of the following markers HLA-I HLA-II CD80, CD86, CD27, CD40L CD62L CCR7, CD54 and CD25. Thus, we have found that the phenotype of the T cell is important.

Vaccine

The invention relates to a method for inducing an immunological response in an individual, particularly a mammal, preferably humans, which comprises inoculating the individual with the antigen-containing T cell of the present invention, such that the antigen produces an antibody and/or T cell immune response to protect said individual from, for example, a tumor or infection, such as a bacterial or viral infection. Also provided are methods whereby such immunological response slows tumor growth or viral or bacterial replication.

Thus, the invention relates to an immunological composition that when introduced into an individual, preferably a human, capable of having induced within it an immunological response, induces an immunological response in such individual. The immunological response may be used therapeutically or prophylactically and may take the form of antibody immunity and/or cellular immunity, such as cellular immunity arising from CTL or CD4+ T cells.

The preparation of vaccines which contain an immunogenic polypeptide(s) as active ingredient(s), is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine.

The vaccine formulation of the invention preferably relates to and/or includes an adjuvant system for enhancing the immunogenicity of the formulation. Preferably the adjuvant system raises preferentially a TH1 type of response.

An immune response may be broadly distinguished into two extreme categories, being a humoral or cell mediated immune responses (traditionally characterised by antibody and cellular effector mechanisms of protection respectively). These categories of response have been termed TH1-type responses (cell-mediated response), and TH2-type immune responses (humoral response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglobulin isotypes including in mice IgG1, IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

Immunomodulators, such as vaccines may be prepared from T cells comprising one or more polypeptides, or even nucleotide sequences, of the present invention. The preparation of immunomodulators which contain an immunogenic polypeptide(s) as active ingredient(s), is known to one skilled in the art. Typically, such immunomodulators are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof.

In addition, if desired, the immunomodulators may contain minor amounts of auxiliary agents such as wetting or emulsifying agents, pH buffering agents, and/or adjuvants which enhance the effectiveness of the immunomodulators. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further examples of adjuvants and other agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

Typically, adjuvants such as Amphigen (oil-in-water), Alhydrogel (aluminum hydroxide), or a mixture of Amphigen and Alhydrogel are used. Only aluminum hydroxide is approved for human use.

The proportion of immunogen and adjuvant can be varied over a broad range so long as both are present in effective amounts. For example, aluminum hydroxide can be present in an amount of about 0.5% of the immunomodulators mixture ($Al_2O_3$ basis). Conveniently, the immunomodulators are formulated to contain a final concentration of immunogen in the range of from 0.2 to 200 μg/ml, preferably 5 to 50 μg/ml, most preferably 15 μg/ml.

After formulation, the immunomodulators may be incorporated into a sterile container which is then sealed and stored at a low temperature, for example 4° C., or it may be freeze-dried. Lyophilisation permits long-term storage in a stabilised form.

The immunomodulators are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the immunomodulators composition is lyophilised, the lyophilised material may be reconstituted prior to administration, e.g. as a suspension. Reconstitution is preferably effected in buffer.

The polypeptides of the invention may be formulated into the immunomodulators as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

Antigen

In general terms an antigen is any substance that is capable of intereacting with an antigen receptor. An antigen binds to a specific antibody to provide a mechanism by which the antigen is recognised and inactivated, in this manner, an antigen complexes with a specific antibody so that the complex can attach itself to specialised immune cells that either internalise the complex to destroy it or release biological mediators such as histamine to produce an allergic/inflammatory response. An immunogen is an antigen that activates immune cells to generate an immune response against itself. Thus, an immunogen is an antigen, but an antigen is not necessarily an immunogen. However, for ease of reference herein the terms antigen and immunogen are generally used interchangeably.

The present invention in general terms relates to a new method of presenting an antigen to the immune system. Some of the factors that determine the immunogenic potential of an antigen, and hence its ability to generate an immune response, include accessibility of an antigenic epitope to immune cell recognition and the route of antigen administration. The present invention provides a system for improving these factors such that the immunogenicity of an antigen is optimised. As a result, someone may be able to receive the equivalent of say two or three doses in just one administration of vaccine. Thus, not only is the efficacy of the vaccine improved, but also patient compliance.

The present invention is applicable to any antigen which is capable of being introduced into a T cell such that the antigen is presented to the immune system, and more particularly an APC. In a particularly preferred embodiment the antigen is introduced into the T cell in the form of a polynucleotide which is capable of being expressed in the T cell.

A wide range of suitable antigens is known. Their sequence may be selected, for example, on the basis of polypeptide sequences known in the literature. For polypeptides which have a partial sequence of a protein with an immunogenic activity, it is possible to establish which peptides are suitable candidates by means of sequence comparison. Preferred candidates are polypeptides whose immunogenicity has already been demonstrated, i.e. polypeptides derived from known immunogens, such as viral or bacterial proteins. Polypeptides of this type preferably exhibit a strong reaction on an MLC test on account of their immunogenicity. The term "protein" includes single-chain polypeptide molecules as well as multiple-polypeptide complexes where individual constituent polypeptides are linked by covalent or non-covalent means. The term "polypeptide" includes peptides of two or more amino acids in length, typically having more than 5, 10 or 20 amino acids.

It will be understood that polypeptide sequences for use in the invention are not limited to particular sequences or fragments thereof or sequences obtained from a particular protein but also include homologous sequences obtained from any source, for example related viral/bacterial proteins, cellular homologues and synthetic peptides, as well as variants or derivatives thereof. Polypeptide sequences of the present invention also include polypeptides encoded by polynucleotides of the present invention.

Thus, the present invention encompasses variants, homologues or derivatives of the amino acid sequences of antigens, as well as variants, homologues or derivatives of the amino acid sequences coded for by the nucleotide sequences of the present invention.

In the context of the present invention, a homologous sequence is taken to include an amino acid sequence which is at least 60, 70, 80 or 90% identical, preferably at least 95 or 98% identical at the amino acid level with a particular sequence. In particular, homology should typically be considered with respect to those regions of the sequence known to be essential for antigenicity rather than non-essential neighbouring sequences. Regions that are conserved across family members should be required to have relatively high homology scores—this assists in defining functional molecules. Regions that are unique or poorly conserved between family members should/may be allowed to have lower score, on a case by case basis—this assists in establishing novelty. This bit by bit approach is in general more useful than an overall homology score. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

The terms "variant" or "derivative" in relation to the amino acid sequences of the present invention includes any substitution of, variation of, modification of, replacement of, deletion of or addition of one (or more) amino acids from or to the sequence providing the resultant amino acid sequence preferably has antigenic activity, preferably having at least 25 to 50% of the activity as the polypeptides presented in the sequence listings, more preferably at least substantially the same activity.

Thus, particular sequences of the invention may be modified for use in the present invention. Typically, modifications are made that maintain the antigenicity of the sequence. Thus, in one embodiment, amino acid substitutions may be made, for example from 1, 2 or 3 to 10, 20 or 30 substitutions provided that the modified sequence retains at least about 25 to 50% of, or substantially the same activity. However, in an alternative embodiment, modifications to the amino acid sequences of a polypeptide of the invention may be made intentionally to reduce the biological activity of the polypeptide. For example truncated polypeptides that remain capable of binding to target molecule but lack functional effector domains may be useful as inhibitors of the biological activity of the full length molecule.

In general, preferably less than 20%, 10% or 5% of the amino acid residues of a variant or derivative are altered as compared with the corresponding region depicted in the sequence listings.

Amino acid substitutions may include the use of non-naturally occurring analogues, for example to increase blood plasma half-life of a therapeutically administered polypeptide (see below for further details on the production of peptide derivatives for use in therapy).

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Polypeptides of the invention also include fragments of full length polypeptides and variants thereof. Preferred fragments include those which include an epitope. Suitable fragments will be at least about 5, e.g. 10, 12, 15 or 20 amino acids in length. They may also be less than 200, 100 or 50 amino acids in length. Polypeptide fragments of the proteins and allelic and species variants thereof may contain one or more (e.g. 2, 3, 5, or 10) substitutions, deletions or insertions, including conserved substitutions. Where substitutions, deletion and/or insertions have been made, for example by means of recombinant technology, preferably less than 20%, 10% or 5% of the amino acid residues depicted in the sequence listings are altered.

Particularly preferred fragments include those having antigenic domains.

Polynucleotides for use in the invention comprise nucleic acid sequences encoding the sequences of the invention. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

Polynucleotides of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention.

The terms "variant", "homologue" or "derivative" in relation to the nucleotide sequence include any substitution of, variation of, modification of, replacement of, deletion of or addition of one (or more) nucleic acid from or to the sequence providing the resultant nucleotide sequence codes for a polypeptide having antigenic activity.

As indicated above, with respect to sequence homology, preferably there is at least 75%, more preferably at least 85%, more preferably at least 90% homology to the sequences shown in the sequence listing herein. More preferably there is at least 95%, more preferably at least 98%, homology. Nucleotide homology comparisons may be conducted as described above. A preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

The present invention also encompasses nucleotide sequences that are capable of hybridising selectively to the antigenic sequences, or any variant, fragment or derivative thereof, or to the complement of any of the above. Nucleotide sequences are preferably at least 15 nucleotides in length, more preferably at least 20, 30, 40 or 50 nucleotides in length.

The term "hybridization" as used herein shall include "the process by which a strand of nucleic acid joins with a complementary strand through base pairing" as well as the process of amplification as carried out in polymerase chain reaction technologies.

Polynucleotides of the invention capable of selectively hybridising to the nucleotide sequences presented herein, or to their complement, will be generally at least 70%, preferably at least 80 or 90% and more preferably at least 95% or 98% homologous to the corresponding nucleotide sequences over a region of at least 20, preferably at least 25 or 30, for instance at least 40, 60 or 100 or more contiguous nucleotides.

The term "selectively hybridizable" means that the polynucleotide used as a probe is used under conditions where a target polynucleotide of the invention is found to hybridize to the probe at a level significantly above background. The background hybridization may occur because of other polynucleotides present, for example, in the cDNA or genomic DNA library being screening. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}P$.

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

In a preferred aspect, the present invention covers nucleotide sequences that can hybridise to an antigenic nucleotide sequence under stringent conditions (e.g. 65° C. and 0.1×SSC {1×SSC=0.15 M NaCl, 0.015 M $Na_3$ Citrate pH 7.0}).

Where the polynucleotide of the invention is double-stranded, both strands of the duplex, either individually or in combination, are encompassed by the present invention. Where the polynucleotide is single-stranded, it is to be understood that the complementary sequence of that polynucleotide is also included within the scope of the present invention.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of known sequences under conditions of medium to high stringency. Similar considerations apply to obtaining species homologues and allelic variants.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site-directed mutagenesis of characterised sequences. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides such as a DNA polynucleotides and probes according to the invention may be produced recombinantly, synthetically, or by any means available to those of skill in the art. They may also be cloned by standard techniques.

When proteins or protein fragments are used, the identity of the processed end product can be demonstrated by chemical analysis or by biological assays (the ability of APCs to stimulate T-cells which are specific to the processed fragments).

In principle, peptide candidates are selected for their suitability as foreign peptides in several stages; generally, the candidates are first tested in a peptide binding test for their binding capacity to an MHC-I molecule, preferably by series of tests.

One suitable method of investigation is, for example, the FACS analysis based on flow cytometry. The peptide is marked with a fluorescent dye, e.g. with FITC (fluorescein isothiocyanate) and applied to tumor cells which express the MHC-I molecule. In the flow, individual cells are excited by a laser of a certain wavelength; the fluorescence emitted is measured and is dependent on the quantity of peptide bound to the cell.

Another method of determining the quantity of peptide bound is the Scatchard blot. Peptide labelled with $I^{125}$ or with rare earth metal ions (e.g. europium) is used for this. The cells are charged at 4° C. with various defined concentrations of peptide for 30 to 240 minutes. In order to determine non-specific interaction of peptide with cells, an excess of unlabelled peptide is added to some of the samples, preventing the specific interaction of the labelled peptide. Then the cells are washed to remove any non-specific cell-associated material. The quantity of cell-bound peptide is then determined either in a scintillation counter using the radioactivity emitted, or in a photometer which is suitable for measuring long-lived fluorescence. The data thus obtained are evaluated using standard methods.

In a second step, candidates with good binding qualities are tested for their immunogenicity.

The immunogenicity of xenopeptides derived from proteins the immunogenic activity of which is unknown may be tested, for example, by the MLC test. Peptides which provoke a particularly violent reaction in this test, which is preferably also carried out in series with different peptides, using as standard a peptide with a known immunogenic activity, are suitable for the purposes of the present invention.

Another possible way of testing MHC-I-binding peptide candidates for their immunogenicity consists in investigating the binding of the peptides to T2 cells. One such test is based on the peculiar nature of T2 cells or RMA-S-cells that they are defective in the TAP peptide transporting mechanism and only present stable MHC-I molecules when they are applied to peptides which are presented in the MHC-I context.

T2 cells or RMA-S cells stably transfected with an HLA gene, e.g. with HLA-A1 and/or HLA-A2 genes, are used for this test. If the cells are acted upon by peptides which are good MHC-I ligands, by being presented in the MHC-I context in such a way as to be recognised as foreign by the immune system, these peptides cause the HLA molecules to appear in significant quantities on the cell surface. Detection of the HLAs on the cell surface, e.g. by means of monoclonal antibodies, makes it possible to identify suitable peptides. Here again, a standard peptide known to have a good HLA- or MHC-binding capacity is appropriately used.

The antigen may be derived from fungi, parasites, bacteria and viruses. Thus, one embodiment of the invention relates to the prevention or treatment of infectious diseases. Examples of infectious diseases to which the present invention may applied include: adenovirus, anthrax, cholera, diphtheria, tetanus, pertussis, malaria, influenza including *Haemophilus influenzae* type B, Hepatitis A, Hepatitus B, encephalitis, measles, mumps, rubella, meningitis such as Meningoccal types A, C, Y and W-135, plague, pneumococcus, rabies, smallpox, salmonella, typhoid, varicella, yellow fever, Rift Valley fever. However, the present invention may also be applicable to use with any new immunogen which becomes available. Indeed, because the present invention improves the presentation of the antigen to the immune system, it may be particularly applicable to diseases and infections which are generally believed to be recalcitrant to a vaccine approach, e.g. HIV.

In a particularly preferred embodiment, the present invention provides a cancer vaccine. Thus the present invention is useful in the treatment of tumors, such as melanoma, prostate, lung, breast and colon cancer and lymphomas.

One of the drawbacks of conveniential cancer treatment such as chemotherapy and radiation is that, in destroying the cancer cells, they also damage some healthy tissue. Cancer vaccines seek to amerliorate these problems. The present invention is particularly applicable to use with tumor-associated antigens. Even though the immune system does not recognise cancer cells as foreign, it has been found that cancer cells do carry particular antigens on their surfaces. These may be unique to individual tumors, shared by several types, or expressed by the normal tissue from which a tumor arises. The present invention is also applicable to antigens associated with the products of genes involved in tumor formation, such as oncogenes and tumor suppressor genes. The present invention is further applicable to viruses which have been associated with cancer, such a hepatitis B virus, which has long been implicated in the development of liver cancer and EBV.

The present invention may be employed following diagnosis of disease or following initial therapy such as surgery or chemotherapy.

Non-limiting examples of tumor antigens which may be employed in the present invention will now be discussed below:

Since the cloning of MAGE-1, the first gene reported to encode a human tumor antigen recognized by T cells, molecular identification and characterization of tumor antigens has mainly been achieved for melanoma. A major reason for this lies in the difficulty of establishing cell lines in vitro from other types of cancer, such lines being necessary to generate tumor-specific CTL lines or clones to be used in the genetic or biochemical approach aimed at molecularly identifying new cancer antigens. More recently, however, new approaches have allowed the discovery of new antigens recognized by T cells even in tumors different from melanoma. Examples from the various antigen categories are given below. However, as discussed above, analogs or artificially modified epitopes may also be used in the present invention. Other antigens, identified by antibodies, may also be used and a large collection of them, as detected by the Serex technology, can be found in the data base of the Institute for Cancer Research (www.licr.org/SEREX.htm). It is of note that many tumor antigens (e.g. MAGE, NY-ESO-1a) are now known to be recognized by both T cells and antibodies in the same cancer patients. In addition, using recent technologies (e.g. subtractive hybridization, representational-difference analysis, microarrays) hundreds of genes are being detected which are preferentially expressed or overexpressed in neoplastic cells as compared with normal counterparts or are expressed in metastatic but not in primary, early lesions (e.g. melanoma, breast cancer, lymphoma, etc.). By using appropriate computers algorithms, a number of new epitopes will be identified that can bind MHC molecules. By applying such approaches, a large array of gene products can be screened for their potential antigenic function. Immunogenic epitopes can be selected through appropriate functional assays. All these may also be useful in the present invention.

Classification of Tumor Antigens

Group 1. Class I HLA-restricted Cancer/testis Antigens.

A milestone in tumor immunology was certainly the cloning of MAGE-1 and the subsequent characterization of the first T-cell-defined antigenic epitope a year later. Those findings were rapidly followed by the identification of new members within this group. The MAGE, BAGE and GAGE families of genes were born. The antigens belonging to this group, now including also NY-ESO-1, were called cancer/testis (CT) antigens for their expression in histologically different human tumors and, among normal tissues, in spermatocytes/spermatogonia of testis and, occasionally, in placenta. These antigens now represent one of the main components for antitumor vaccine development. CT antigens result from reactivation of genes normally silent in adult tissues, but that are transcriptionally activated in some tumors. CT genes are probably the most characterized ones. New genes in the group of CT antigens which have been cloned will include (CT9, CT10, LAGE, MAGE-B5, -B6, -C2, -C3 and-D, HAGE, SAGE).

Group 2. Class I HLA-restricted Differentiation Antigens.

These antigens are shared between tumors and the normal tissue from which the tumor arose; most are found in melanomas and normal melanocytes. Many of these melanocyte lineage-related proteins are involved in the biosynthesis of melanin. Epitopes recognized by both CD8+ and CD4+ T cells can be derived from melanosome proteins.

Group 3. Class I HLA-restricted Widely Expressed Antigens.

Genes encoding widely expressed tumor antigens have been detected in many normal tissues as well as in histologically different types of tumors with no preferential expression on a certain type of cancer. It is possible that the many epitopes expressed on normal tissues are below the threshold level for T-cell recognition, while their overexpression in tumor cells can trigger an anticancer response even by breaking a previously established tolerance. These widely expressed gene products have revealed a broad spectrum of mechanisms that are involved in generating T-cell-defined epitopes through alterations in gene transcription and translation. To highlight some examples, the epitope of CEA is derived from a non-AUG-defined alternative ORF, while the RU2 gene creates its epitope by reverse strand transcription.

Group 4. Class I HLA-restricted, Tumor-specific Antigens.

Unique tumor antigens arise from point mutations of normal genes (like-catenin, CDK4), whose molecular changes often accompany neoplastic transformation or progression. These antigens are thus expressed only in the individual tumor where they were identified since it is unlikely that the same mutation may occur in two different neoplasms unless it involves genes (e.g. RAS) whose alteration is an obligatory step in neoplastic transformation. In mouse models unique antigens have been shown to be more immunogenic than the other groups of shared antigens; since unique antigens are responsible of the rejection of tumor transplants in mice, they have been defined as tumor-specific transplantation antigens (TSTA).

Other tumor-specific but shared antigens have been described which are generated by alteration in splicing mechanisms and which occur in tumor but not in normal cells, as in the case of TRP-2/INT2.

Group 5. Class II HLA-restricted Antigens.

Stimulation of the CD4+ T helper cells by tumor antigens is considered to be impaired or absent in cancer patients and this may be the reason of an insufficient immune response to tumors. Therefore the identification of tumor antigen epitopes recognized by such lymphocytes is a crucial step in the long sought improvement of antitumor immune response that may result into clinical efficacy. The first epitope presented by a class II HLA and capable of provoking a CD4+ T-cell response was identified in 1994 in melanoma tyrosinase. Then a gap of 4 years followed during which only one additional epitope was characterized, before other genes encoding class II-restricted peptides were discovered. However, as the technical and methodological approaches for identifying CD4+ T-cell epitopes of tumor antigens have become available, an exponential increase in reporting such epitopes has been seen. In fact, since 1998 as many as 27 new class II HLA-restricted epitopes from 14 antigens have been molecularly identified using, among others, Ii-cDNA fusion libraries, immunized transgenic mice and biochemical approaches. It is of note that even class II-restricted antigens include a subgroup of mutated proteins which, therefore, represent truly tumor-specific antigens.

Group 6. Fusion Proteins.

In several malignancies, particularly in some forms of leukemias, the molecular mechanism of carcinogenesis involves translocation of chromosomes which results in fusion of distant genes. This often causes the synthesis of fusion proteins which characterize each type of disease (e.g. bcr-abl, pml-RAR in CML and APL, respectively) and generate new epitopes that can be recognized by T cells, either CD8+ or CD4+ in class I or class II HLA restriction, respectively. Although these epitopes appear to be weakly immunogenic in leukemia patients, some of these peptides or proteins can nevertheless be used to pulse dendritic cells for vaccination.

Non-limiting examples of tumor antigens which are particularly useful in the present invention include: MAGE, BAGE and GAGE, CTL recognising epitopes from tyrosinase, MelanA$^{Mart1}$, gp100$^{me17}$ and gp75$^{TRP1}$.

Selection Gene or Marker

The T cell of the present invention preferably comprises at least one further foreign gene which is a selection gene, or a marker gene. As is well known selection genes may be used to select transformed cells from non-transformed cells. Many different selectable markers have been used successfully in vectors, and these may equally well be used in the present invention. Suitable, bacterial or animal antigens are used. In a preferred embodiment, for instance bacterial antigens (e.g.

β-galactosidase), bacterial genes or other genes conferring resistance to antibiotics (e.g. neo, amp, Kan and tet) or a suicide gene (e.g. HSV-Tk).

In a preferred embodiment, the T cell comprises at least a suicide gene as the further foreign antigen. The advantage offered by the use of such a suicide gene is that the activation of this gene can be controlled by systemically administering a further substance such as cyclosporin or 5'-fluorocytosin. An examples of a suicide gene includes the herpes simplex virus thymidine kinase gene (HSV Tk) which can kill infected and bystander cells following treatment with ganciclovir.

Other suicide genes include, for example, the cytosine deaminase gene which confers lethal sensitivty to 5-fluorocytosine and the human cell surface molecule CD20, which allows killing of the transduced cells by administration of rituximab (*Introna et al. Hum Gene Ther* 11:611, 2000). The advantage of CD20 is that being a human molecule it is not immunogenic.

A particular advantage of the use of a suicide gene is safety in that the it can be used for killing the T cell if undesired side effects occur.

According to a particularly preferred embodiment of the present invention the selection or marker gene is itself immunogenic or expresses a protein which is immunogenic. The advantage of such a system is that enables the immunological status of the patient, and therefore the effectiveness of the vaccination treatment to be monitored. Examples of such suitable further foreign antigens include HSV-Tk and Neo, both of which generate an immune response in an immunocompetent patient. For example, immnisation of the patient against the first antigen can be monitored by detecting anti-HSV-Tk cytolytic activity as is described in more detail below.

For safety reasons, the T cells of the present invention may also be growth-arrested, e.g. thorugh irradiation or treatment with mitomycin. Such irradiation may be carried out at room temperature at a dose of 100 Rad/minute. Cells exposed to such irradiation no longer proliferate, but on account of their mRNA which is still present in the cell, are still capable of expressing proteins.

Treatment

This includes any therapeutic application that can benefit a human or non-human animal. The treatment of mammals is particularly preferred. Both human and veterinary treatments are within the scope of the present invention.

Treatment may be in respect of an existing condition or it may be prophylactic. It may be of an adult, a juvenile, an infant, a foetus, or a part of any of the aforesaid (e.g. an organ, tissue, cell, or nucleic acid molecule).

The T cells prepared by the method of the invention may be administered to a patient suffering from a malignancy.

Generally, in an ex vivo approach the patient will be the same patient from whom the treated T cells originated. Examples of malignancies that may be treated include cancer of the breast, cervix, colon, rectum, endometrium, kidney, lung, ovary, pancreas, prostate gland, skin, stomach, bladder, CNS, oesophagus, head-or-neck, liver, testis, thymus or thyroid. Malignancies of blood cells, bone marrow cells, B-lymphocytes, T-lymphocytes, lymphocytic progenitors or myeloid cell progenitors may also be treated.

The tumor may be a solid tumor or a non-solid tumor and may be a primary tumor or a disseminated metastatic (secondary) tumor. Non-solid tumors include myeloma; leukaemia (acute or chronic, lymphocytic or myelocytic) such as acute myeloblastic, acute promyelocytic, acute myelomonocytic, acute monocytic, erythroleukaemia; and lymphomas such as Hodgkin's, non-Hodgkin's and Burkitt's. Solid tumors include carcinoma, colon carcinoma, small cell lung carcinoma, non-small cell lung carcinoma, renal carcinoma, adenocarcinoma, melanoma, basal or squamous cell carcinoma, mesothelioma, neuroblastoma, glioma, astrocytoma, medulloblastoma, retinoblastoma, sarcoma, osteosarcoma, rhabdomyosarcoma, fibrosarcoma, osteogenic sarcoma, hepatoma, and seminoma.

Typically the composition of the present invention may be administered with a tumor-specific antigen such as antigens which are overexpressed on the surface of tumor cells.

The T cells may be used to treat an ongoing immune response (such as an allergic condition or an autoimmune disease) or may be used to generate tolerance in a patient. Thus the cells of the present invention may be used in therapeutic methods for both treating and preventing diseases characterised by inappropriate lymphocyte activity in animals and humans. The T cells may be used to confer tolerance to a single antigen or to multiple antigens.

Typically, T cells are obtained from the patient or donor and primed as described above before being returned to the patient (ex vivo therapy).

Pharmaceutical Compositions

A pharmaceutical composition is a composition that comprises or consists of a therapeutically effective amount of a pharmaceutically active agent. It preferably includes a pharmaceutically acceptable carrier, diluent or excipients (including combinations thereof). Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

"Therapeutically effective amount" refers to the amount of the therapeutic agent which is effective to achieve its intended purpose. While individual patient needs may vary, determination of optimal ranges for effective amounts of each nitric oxide adduct is within the skill of the art. Generally the dosage regimen for treating a condition with the compounds and/or compositions of this invention is selected in accordance with a variety of factors, including the type, age, weight, sex, diet and medical condition of the patient, the severity of the dysfunction, the route of administration, pharmacological considerations such as the activity, efficacy, pharmacokinetic and toxicology profiles of the particular compound used, whether a drug delivery system is used, and whether the compound is administered as part of a drug combination and can be adjusted by one skilled in the art. Thus, the dosage regimen actually employed may vary widely and therefore may deviate from the preferred dosage regimen set forth herein.

Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

The dosage range required depends on the choice of peptide, the route of administration, the nature of the formulation, the nature of the subject's condition, and the judgement of the attending practitioner. Suitable dosages, however, are in the range of 0.1-100 μg/kg of subject.

A vaccine composition is conveniently in injectable form. Conventional adjuvants may be employed to enhance the immune response. A suitable unit dose for vaccination is 0.5-5 microgram/kg of antigen, and such dose is preferably administered 1-3 times and with an interval of 1-3 weeks. With the indicated dose range, no adverse toxicological effects will be observed with the compounds of the invention which would preclude their administration to suitable individuals.

Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimisation, as is well understood in the art.

Preferred features and embodiment of the present invention will now be described further with reference to the following Examples and Figures.

EXAMPLES

Example 1

Figure 1:
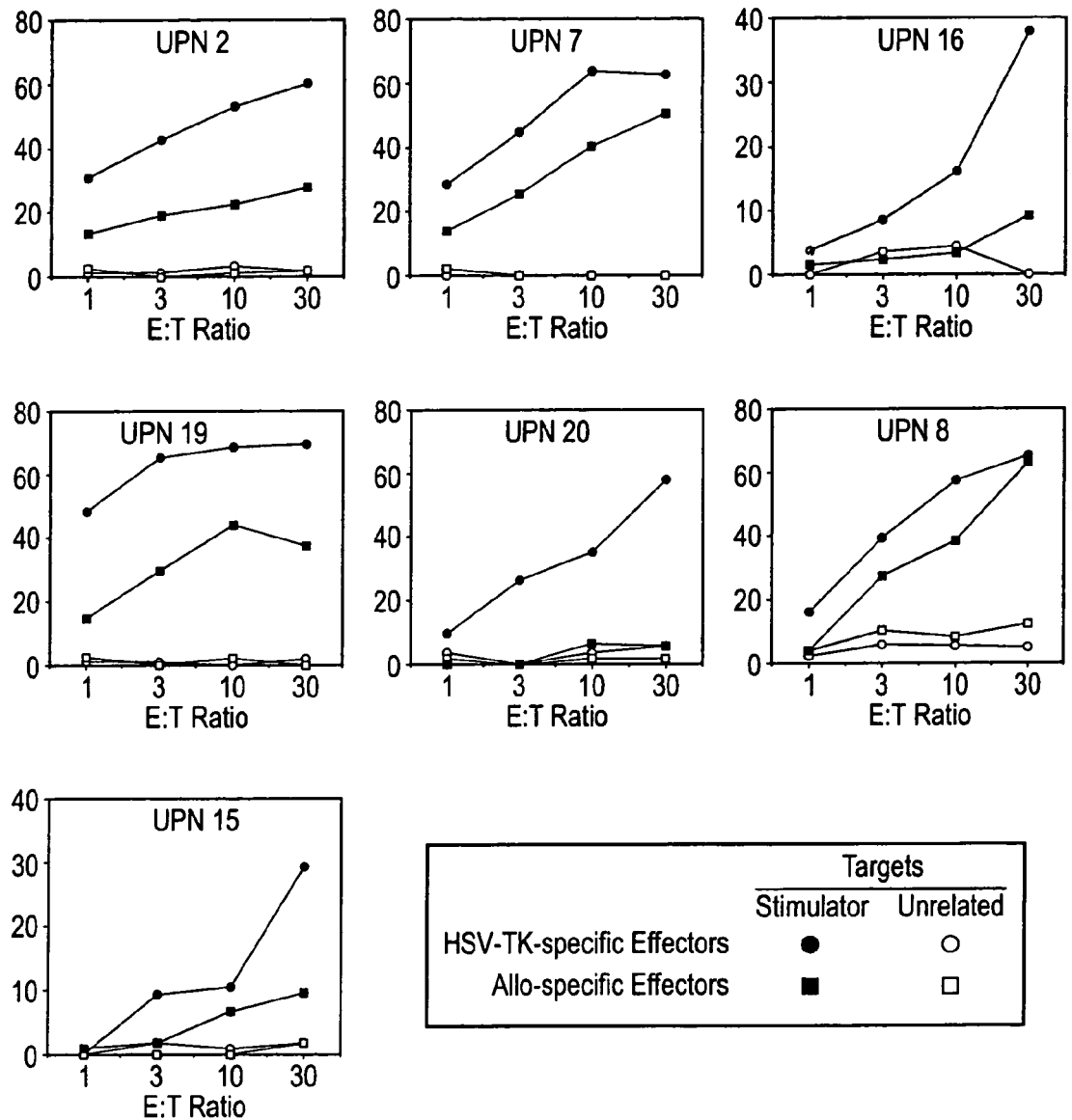
FIG. 1 presents results of cell lysis experiments using effector cells isolated from the infused patients against stimulator cells (full symbol) and against unrelated targets (empty symbols). Effector cells were generated by the stimulation of peripheral blood mononuclear cells (PBMC) isolated from 7 treated patients with autologous transduced T cells (circle) and with allogeneic T cells (square). Transduction was performed with vectors encoding the HSV-Tk protein and the cell surface marker ΔLNGFr (deleted human low affinity nerve growth factor receptor).

The infusion of donor lymphocytes in the context of allogeneic bone marrow transplantation (allo-BMT) for leukaemia is an established strategy to control tumor relapse and viral infections. To circumvent the inherent risk of graft-vs-host disease (GVHD) BM-donor lymphocytes can be transduced by a suicide gene, conferring sensitivity to a drug, that may allow the selective elimination of the transduced cells for both therapeutic and safety issues.

Peripheral blood mononuclear cells (PBMC) were isolated by Lymphoprep (Nycomed, Oslo, Norway) density-gradient centrifugation from all the BM-donors and the healthy controls studied.

Activation. Two different activation signals were used to activate T cells (hereafter referred to as T blasts): phytoemoagglutinine (PHA) 2 μg/ml (Boehringer Mannheim); anti-CD3 mAb (OKT3) 30 ng/ml (Orthoclone, Milan, Italy); OKT3 (30 ng/ml). Activated T cells were cultured at $1\times10^6$ cells/ml, in RPMI 1640 supplemented with 5% autologous serum in the presence of hu-r-IL-2 100 U/ml (EuroCetus Italia S.r.l., Milan, Italy). Culture medium was changed every 3-4 days.

Transduction. Two methods of lymphocyte transduction were utilized. 1-coculture: Lymphocyte activation was performed on a semiconfluent monolayer of lethally irradiated packaging cells (100 Grays; GIL RAD, Gilardoni, Mandello, Italy), in tissue culture flasks in the presence of polybrene (8 μg/ml). The cocultivation was performed for 72 hours. 2-spinoculation: After 3-4 days of activation lymphocytes were recovered and transduced by 2 cycles of 2 hours-centrifugation in the presence of cell free retroviral supernatants and polybrene (8 μg/ml).

After the transduction procedures, lymphocytes were harvested and seeded in fresh medium ($10^6$/ml). Retroviral transduced cells were analyzed for ΔLNGFr expression on day 5 by FACS with the mouse-anti-human LNGFR mAb 20.4 (ATCC, Rockville, Md.).

Selection. Pure populations of transduced cells were obtained by two selection methods. Lymphocytes transduced with the SFCMM2 vector, encoding the HSV-TK/neo (TN) fusion protein, a bifunctional protein conferring both the -neomycin resistance and the HSV-TK activity, were selected by the addition of neomycin (0,8 μg/ml) to the culture medium. Fresh neomycin was added at day 3, 7 and 10 of culture. Lymphocytes transduced with the SFCMM3 vector, encoding the wild type HSV-TK and the ΔLNGFr were immunoselected by magnetic sorting with the mAb 20.4 and rat anti-mouse-IgG1 coated beads (Dynabeads M-450, Dynal A.S. N0212 Oslo, Norway).

Pure populations of transduced cells were frozen and then administered to the patients or utilized ex vivo as stimulator to monitor antigen-specific immune responses.

Samples of PBMCs were taken from the 7 treated patients, and contacted to either irradiated transduced T cells of the respective BM-donor, or irradiated allogeneic T blasts. After 2 days of culture 10 U/ml of IL2 were added. The mixtures were observed for lysis of the stimulator cells, which indicated that cytotoxic T lymphocytes (CTLs) specific for a transgene product expressed by the transduced T cells or for an alloantigen were present in the samples. The lysis assay employed was a chromium release assay. The results presented in FIG. 1 show that cytotoxic T cells with specificity for the transduced targets were obtained from all the patients. To assess the patients' immunocompetence, specific immune response against allogeneic targets was tested and detected in all the responders. This suggests that infusion of T blasts, transduced under the conditions described above, are able to elicit immune responses against the transduced cells.

Example 2

Figure 2:
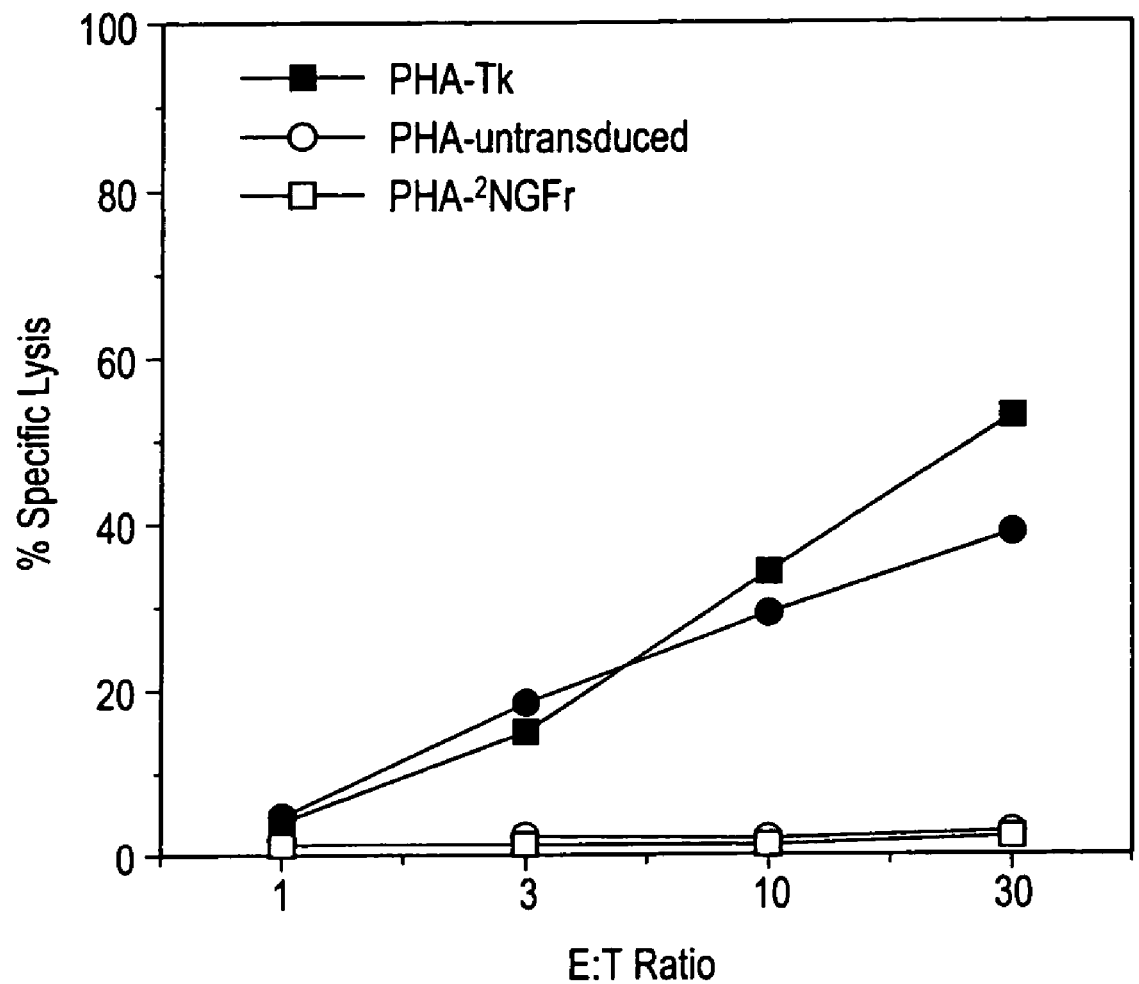
FIG. 2 presents results of cell lysis experiments using effector cells isolated from a treated patient against unmodified cells and cells expressing either HSV-Tk or ΔLNGFr.
Figure 3:
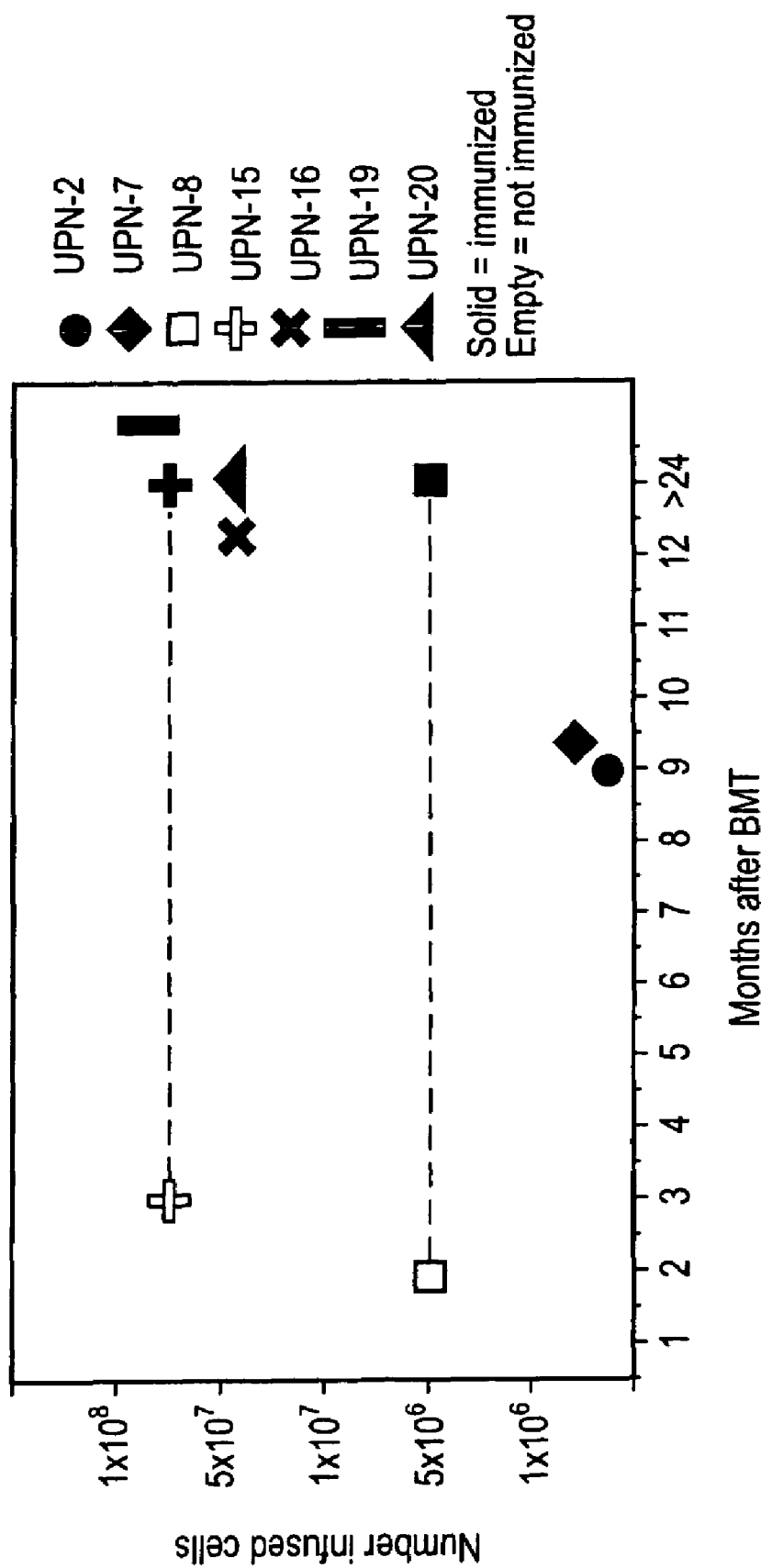
FIG. 3 shows the relation between infusions' time, number of engineered T cells injected and the development of a transgene-specific immune response. Data points represent the cell infusion responsible (full symbols) or not responsible (empty symbols) for the induction of the immune response.

Further studies were carried out to identify the target antigens of the immune response. Effector cells derived from one of the patient were tested against autologous T blasts expressing single components of the vector. T blasts expressing HSV-TK were lysed while target cells expressing the ΔLNGFr were not recognized at all (FIG. 2). Analogous results were obtained with effector cells isolated from other patients.

Example 3

The results from Example 1 (i.e. generation of HSV-TK-specific immunity) were analyzed in relation to the time of the infusions and the number of engineered T cells infused. Time of the infusions, measured as months from bone marrow transplantation (abscissa) and number of engineered T cells injected (ordinate), are presented. The development of an immune response against the transduced cells was evaluated by ex vivo stimulation of PBLs against autologous-transduced and allogeneic T cells as described in example 1. In the presence of a positive anti-allo immune response the patient was considered not immunized (empty symbols) or immunized (full symbols) to the transgene depending on the presence of a cytolytic activity against the transduced cells. Data points represent the cell infusion responsible (full symbols) or not responsible (empty symbols) for the induction of the immune response. For patient UPN-15 two different time points are represented. These results suggested that induction of the immune response by the in vitro manipulated cells was independent of the number of infused cells and strictly related to the presence of a functional immune system at the time of the infusion.

Example 4

Figure 4:
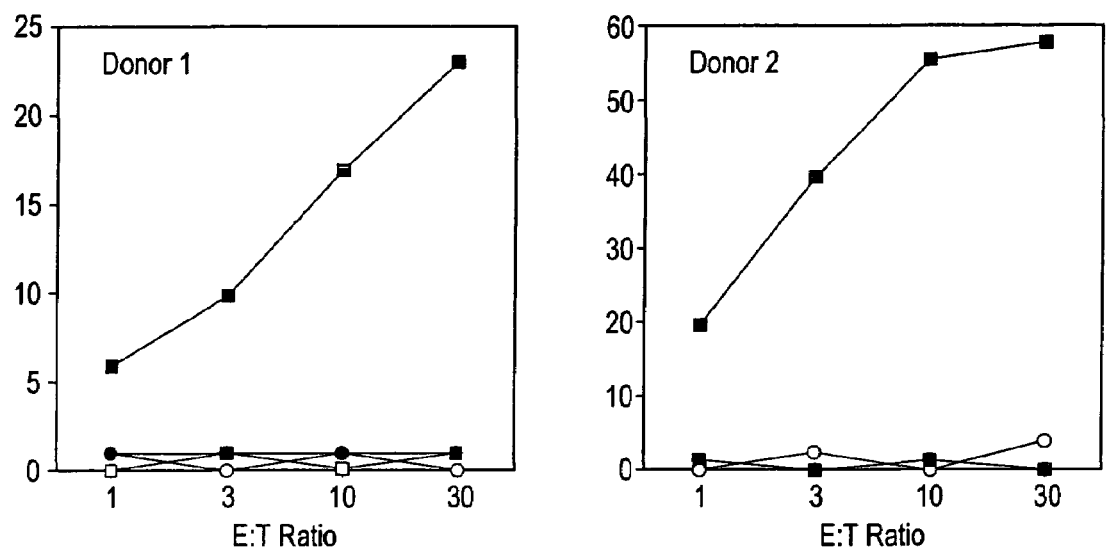
FIG. 4 presents results of cell lysis experiments using effector cells isolated from two healthy donors against the stimulator cells (full symbol) and against unrelated targets (empty symbols). Effector cells were generated by the stimulation of PBMC isolated from 2 healthy donors with autologous transduced T cells (circle) and with allogeneic T cells (square).
Figure 4:
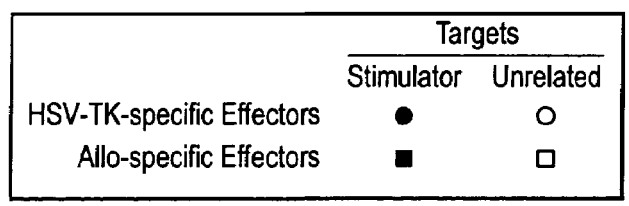

Further studies were carried out to identify the mechanism utilized by the transduced T blasts to elicit in vivo a transgene-specific immune response. Samples of PBMCs were taken from 2 healthy donors and were stimulated accordingly to example 1 with either irradiated autologous transduced T blasts, or irradiated allogeneic T blasts. After 2 days of culture 10 U/ml of IL2 were added. The mixtures were observed for lysis of the stimulator cells, which indicated that CTLs specific for a transgene product expressed by the transduced T blasts or for an alloantigen were present in the samples. The results presented in FIG. 4 show that cytotoxic T cells with specificity for the transduced targets were not obtained from healthy controls. Thus suggesting that in our experimental setting transduced T blasts are not able to act as professional antigen presenting cells, activating by themselves naive T cell precursors. An in vivo cross-presentation pathway, mediated by resident APCs, could be responsible for the induction of the transgene-specific immune response in vivo in the infused patients.

Example 5

Figure 5:
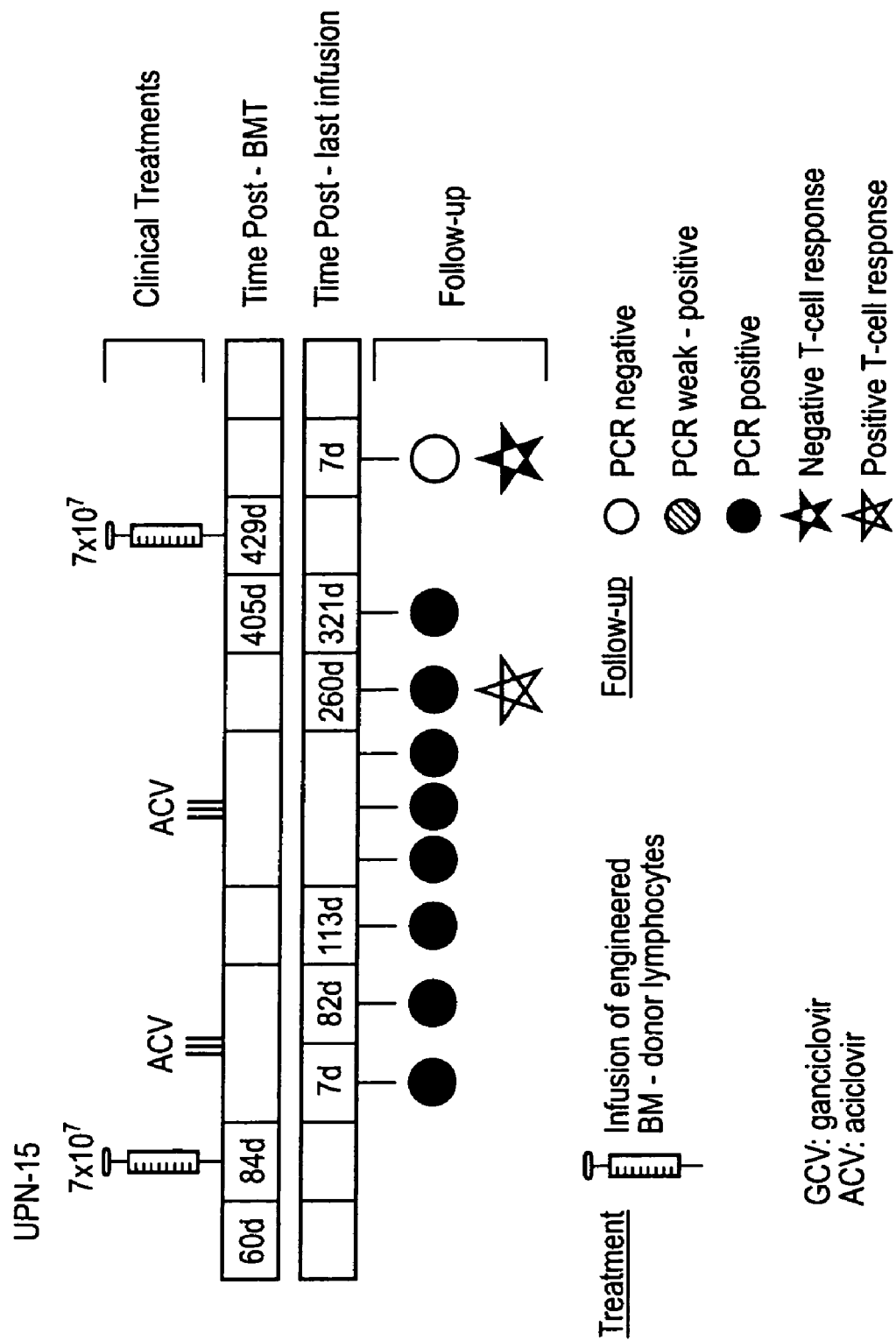
FIG. 5 shows a schematic representation of the clinical history and follow-up of patient UPN-15. The presence (full circle) or the absence (empty circle) of circulating transduced T cells was monitored at the indicated time points by PCR with HSV-Tk-specific primers. The development of an immune response was monitored by ex vivo stimulation of circulating lymphocytes against autologous-transduced and allogeneic T cells. The patient was considered not immunized (empty stars) or immunized (full stars) against the transgene depending on the anti-HSV-Tk cytolytic activity detected.

Further experiments were carried out to define the cellular mechanism responsible for the induction of the transgene-specific immune response. The ability to generate effective immune responses and the presence of circulating transduced T blasts were evaluated during the follow-up of patient UPN-15 (FIG. 5). The presence of circulating transduced T blasts was analysed by PCR with HSV-TK-specific primers, on fresh blood samples. Immune reconstitution and HSV-TK-specific immunization were evaluated as described in example 1. Patient UPN-15 was injected early after transplant in the absence of a functional immune system. The infused cells were detected by PCR in the circulation for a long time (FIG. 5 full circles), even when his immune system was fully reconstituted. Immunological reconstitution was documented by the presence of an active anti-allo immune repertoire in the absence of an HSV-TK specific immune response (FIG. 5 empty star). Therefore, at the time of the injection the immunization does not occur because the capacity of the patient to generate an adequate T cell response is profoundly compromised in term of both antigen-presenting and antigen-responding capabilities. Later on, when the immune system is fully reconstituted, the circulating transduced T blasts are unable to provide activation signals, they do not act act as APC and therefore, cytotoxic effector cells specific for the transduced cells can not be elicited.

A second injection of HSV-TK-engineered T blasts, performed when the UPN-15's immune system was fully reconstituted, resulted in the induction of a HSV-TK-specific immunity (FIG. 5 full star) leading to the destruction of the engineered cells (FIG. 5 empy circle).

Therefore, immunization occurs when T cells manipulated as described in example 1, are delivered in an immunocompetent melieu. In particular, T cells act in vivo as a vehicle carrying the antigen in the right place to induce an immune response. Here, the partial cell death of the injected cells, mediated by growth factor (i.e. IL2) deprivation, leads to the release of the carried antigens; this is followed by presentation of the released antigenic material by host APC and activation of naive HSV-TK-specific T cell precursors.

The foregoing experiments described a new methodology whereby T lymphocytes can be in vitro modified to become the vehicle for target antigen delivery in vivo.

Example 6

T lymphocytes can be in vitro modified to become the vehicle for target antigen delivery in vivo. Autologous lymphocytes from a patient affected by a MAGE-3 positive melanoma, have been transduced by a retroviral vector encoding the tumor antigen MAGE-3 and the HSV-TK/neo (TN) fusion protein, a bifunctional protein conferring both the neomycin resistance and the HSV-TK activity.

The activation transduction and selection procedures utilized were the same reported in Example 1. At the end of the manipulation process, pure populations of transduced cells were frozen and then administered to the patients with an escalating dose protocol of vaccination. The transduced cells were also utilized ex vivo as stimulators to monitor antigen-specific immune responses.

Figure 6:
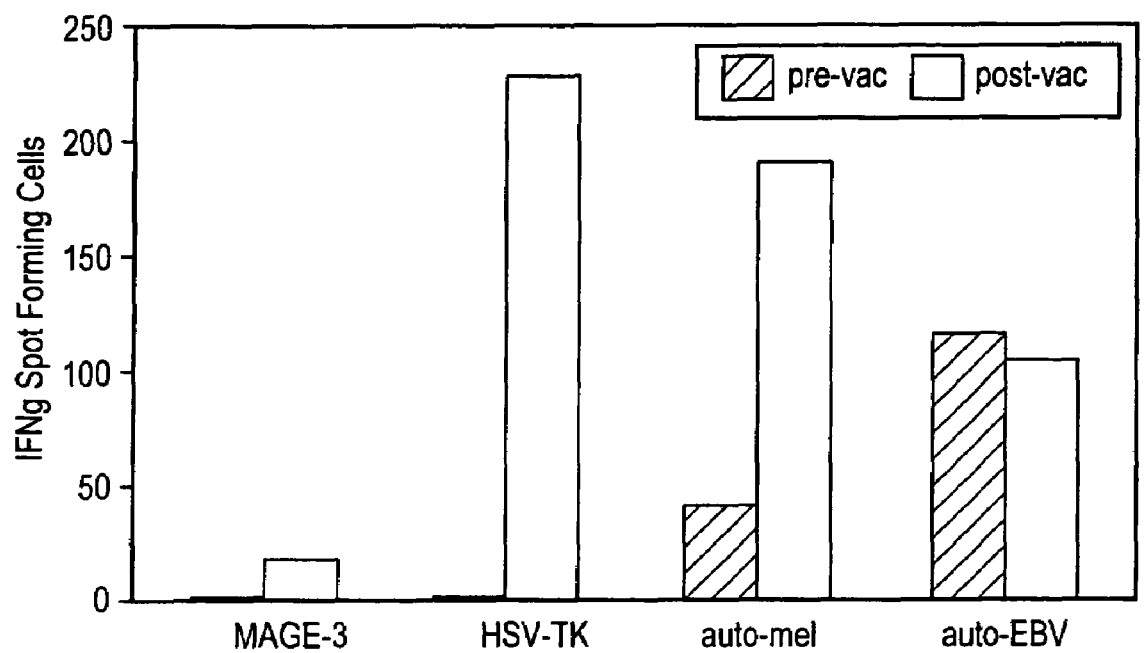
FIG. 6 shows the results of ELISPOT experiments using fresh lymphocytes isolated from a treated melanoma patient, against autologous cells expressing either MAGE-3 or HSV-Tk and against unmodified autologous EBV and melanoma cell lines.

Samples of PBMCs were taken from the melanoma patient before treatment and after the fifth vaccination. The collected cells were immediately contacted to autologous EBV melanoma cells, and EBV transduced with either MAGE-3 or HSV-TK. The test was performed on ELISPOT-plates coated with anti-IFNg mAb. After 24 h of culture the cells were removed and the plates were treated to evaluate the presence of IFNg spots. The results presented in FIG. 6 show that IFNg-releasing T cells with specificity for the transgenes (i.e. MAGE-3 and HSV-TK) were obtained after the vaccination. A significant increase in the frequency of tumor-specific T cells was also detected. This suggests that infusion of T blasts, transduced under the conditions described above, are able to elicit immune responses against the transduced cells.

Example 7

Figure 7:
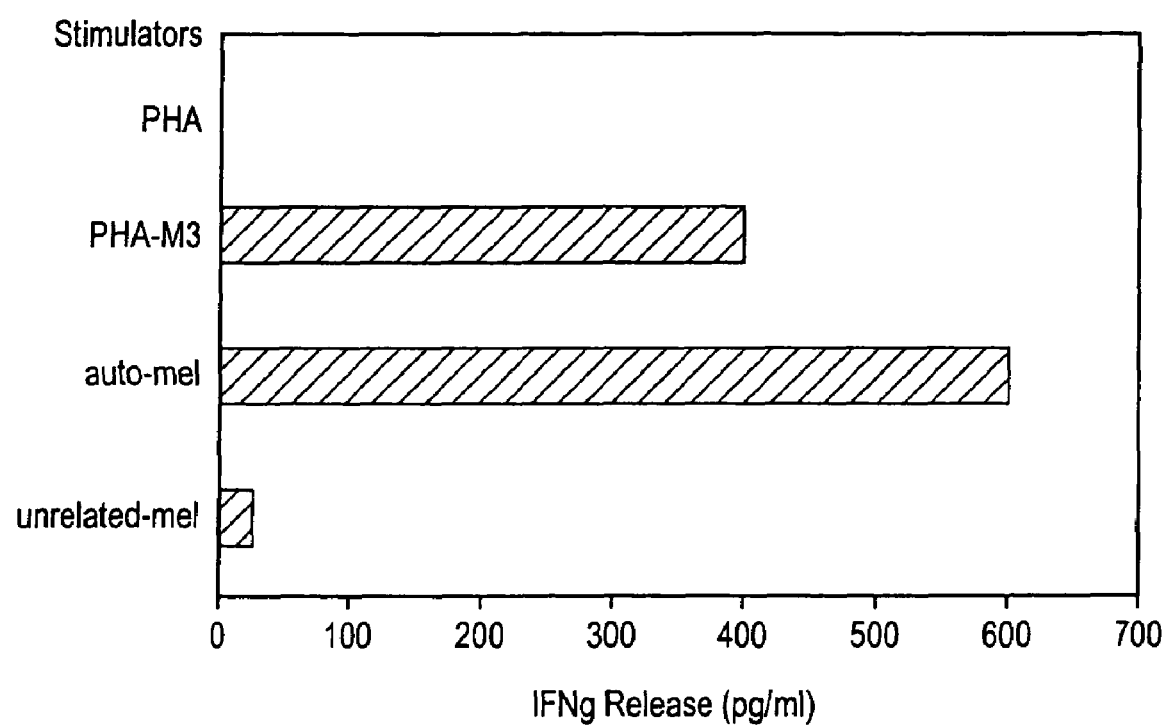
FIG. 7 shows the results of IFNg release experiments using effector cells isolated in vitro from a treated melanoma patient, against either MAGE-3 transduced and untransduced T cells (i.e. PHA-M3 and PHA) respectively, and autologous and unrelated melanoma cell lines. Effector cells were generated by the stimulation of PBMC isolated from the treated patient with autologous MAGE-3 transduced T cells.

PBMCs were taken from the melanoma patient after the vaccinations and contacted to irradiated MAGE-3-transduced T cells. After 2 days of culture 10 U/ml of IL2 were added. The mixtures were observed for IFNg release in the presence of the stimulator cells, which indicated that effector cells specific for the MAGE-3 transgene product expressed by the transduced T cells were present in the samples. The results presented in FIG. 7 show that effector T cells with specificity for MAGE-3 and the autologous tumors were obtained. This further confirms that infusion of T blasts, transduced under the conditions described above, are able to elicit immune responses against the transgene products.

Example 8

To investigate the kinetics of generation of transgenes-specific immune effectors, in respect of the dose of transduced cells infused, PBMCs were taken from the melanoma patient before treatment and at several time-points of the vaccination protocol (i.e. after 3, 5 and 15 vaccination). The collected cells were contacted with either irradiated MAGE-3-transduced or HSV-TK-transduced T cells. After 2 days of culture 10 U/ml of IL2 were added. For each time-point several independent micro-cultures were plated (ranging from 30 to 48). After several rounds of stimulations the micro-cultures were observed for IFNg release in the presence of the stimulator cells, which indicates that effector cells specific for MAGE-3 or HSV-TK were present in the samples. The results summarized in the following table show the existence of a correlation between injection of transduced T cells and development of an immune response against the transgenes. A continuous increase of the amount of MAGE-3 reactive T cell precursors, represented by the number of positive micro-cultures, was observed

| In vivo infusion of MAGE-3-expressing T cells is responsible for the induction of MAGE-3-specific immune responses. | | |
|---|---|---|
| | No of micro-cultures with specific activity | |
| Blood Sample | anti-MAGE-3 | anti-HSV-TK |
| Pre-treatment | 0 | 0 |
| Post-3 | 3/42 | ND |
| Post-5 | 6/48 | 48/48 |
| Post-15 | 30/30 | ND |

ND: not done

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the following claims.

The invention claimed is:

1. An isolated T cell transduced with a nucleic acid encoding and expressing a tumor associated antigen, wherein said T cell is capable of delivering the antigen to an antigen presenting cell for subsequent presentation by the antigen presenting cell, or said T cell is capable of delivering the antigen to a lymph node.

2. The isolated T cell according to claim 1, wherein the T cell comprises a marker.

3. The isolated T cell according to claim 2, wherein the marker is a marker gene.

4. The isolated T cell according to claim 3, wherein the marker gene is a bacterial resistance gene.

5. The isolated T cell according to claim 4, wherein the bacterial resistance gene confers neomycin resistance.

6. The isolated T cell according to claim 3, wherein the marker gene further encodes another antigen.

7. The isolated T cell according to claim 6, wherein the antigen is HSV-Tk or CD20.

8. The isolated T cell according to claim 2, wherein the marker comprises a nucleic acid another antigen and a bacterial resistance gene.

9. A pharmaceutical composition comprising the isolated T cell of any one of claims 1 and 2-8.

10. The pharmaceutical composition according to claim 9, wherein said composition is an immunogenic composition.

11. The pharmaceutical composition of claim 10, further comprising an adjuvant.

* * * * *